United States Patent
Rudser

(10) Patent No.: US 10,751,455 B2
(45) Date of Patent: Aug. 25, 2020

(54) PATIENT BEHAVIOR SENSITIVE CONTROLLER

(71) Applicant: HeartWare, Inc., Miami Lakes, FL (US)

(72) Inventor: John Rudser, Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 248 days.

(21) Appl. No.: 15/825,602

(22) Filed: Nov. 29, 2017

(65) Prior Publication Data
US 2018/0147333 A1  May 31, 2018

Related U.S. Application Data

(60) Provisional application No. 62/428,130, filed on Nov. 30, 2016.

(51) Int. Cl.
| | | |
|---|---|---|
| *A61M 1/10* | (2006.01) | |
| *A61M 1/12* | (2006.01) | |
| *G06F 19/00* | (2018.01) | |
| *A61B 5/00* | (2006.01) | |

(52) U.S. Cl.
CPC .......... *A61M 1/1086* (2013.01); *A61M 1/122* (2014.02); *G06F 19/3456* (2013.01); *A61B 5/0031* (2013.01); *A61B 5/4839* (2013.01); *A61M 1/101* (2013.01); *A61M 1/127* (2013.01); *A61M 2205/3523* (2013.01); *G06F 19/3418* (2013.01)

(58) Field of Classification Search
CPC ............... A61M 1/1086; A61M 1/122; A61M 2205/3523; A61M 1/127; A61M 1/101; G06F 19/3456; G06F 19/3418; A61B 5/4839; A61B 5/0031
See application file for complete search history.

(56) References Cited

U.S. PATENT DOCUMENTS

| | | |
|---|---|---|
| 6,234,772 B1 | 5/2001 | Wampler et al. |
| 6,264,635 B1 | 7/2001 | Wampler et al. |
| 7,699,586 B2 | 4/2010 | LaRose et al. |

(Continued)

FOREIGN PATENT DOCUMENTS

| | | |
|---|---|---|
| WO | 2015183922 A1 | 12/2015 |
| WO | 2016137743 A1 | 9/2016 |
| WO | 2017079111 A1 | 5/2017 |

OTHER PUBLICATIONS

International Search Report and Written Opinion dated Mar. 12, 2018, for corresponding International Application No. PCT/US2017/063621; International Filing Date: Nov. 29, 2017 consisting of 11-pages.

*Primary Examiner* — Mark Bockelman

(74) *Attorney, Agent, or Firm* — Christopher & Weisberg, P.A.

(57) ABSTRACT

A method of controlling an implantable blood pump of a living patient. The method includes receiving one or more pump signals indicating at least one from the group consisting of a motor speed of the blood pump, power supplied to the blood pump, and differential pressure exerted by the blood pump. One or more medication signals is received indicating whether the patient has taken a medication. The flow rate of blood based on a combination of the one or more pump signals and the medication signals is determined. At least one from the group consisting of increasing and decreasing power is supplied to the pump in response to the determined flow rate.

12 Claims, 5 Drawing Sheets

(56) References Cited

U.S. PATENT DOCUMENTS

| | | |
|---|---|---|
| 8,512,013 B2 | 8/2013 | LaRose et al. |
| 8,864,644 B2 | 10/2014 | Yomtov |
| 2009/0112312 A1 | 4/2009 | LaRose et al. |
| 2012/0245681 A1 | 9/2012 | Casas et al. |
| 2014/0100413 A1 | 4/2014 | Casas et al. |
| 2014/0357937 A1 | 12/2014 | Reyes et al. |
| 2017/0112985 A1 | 4/2017 | Yomtov |

PATIENT BEHAVIOR SENSITIVE CONTROLLER

CROSS-REFERENCE TO RELATED APPLICATION

This application is related to and claims priority to U.S. Provisional Patent Application Ser. No. 62/428,130, filed Nov. 30, 2016, entitled PATIENT BEHAVIOR SENSITIVE CONTROLLER, the entirety of which is incorporated herein by reference.

STATEMENT REGARDING FEDERALLY SPONSORED RESEARCH OR DEVELOPMENT n/a

TECHNICAL FIELD

The present invention relates to a method and system for determining flow rate through an implantable blood pump of a patient taking medication.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD."

A VAD is a device which is used to assist the heart of a mammalian subject such as a human or animal patient. A typical VAD includes a pump which is implanted in the body of the patient. The pump typically has an inlet connected to a source of blood to be circulated, and an outlet connected to an artery. Where a VAD is used to assist the pumping action of the left ventricle, the device draws blood from the left ventricle of the heart and discharges the blood into the aorta. VADs can be used to assist the heart of patients suffering from conditions which impair the pumping ability of the heart. Such assistance can be provided permanently, or while the patient awaits a suitable heart transplant. In other cases, the assistance provided by the VAD allows the heart to heal.

The blood pump may be a miniature rotary impeller pump having an impeller disposed in a pump housing and driven in rotation by a small electric motor which may be closely integrated with the pump. The motor in turn typically is powered by an implantable and/or external power sources such as storage batteries with an arrangement for charging the batteries from an external AC or DC power source. The VAD typically includes a control system which controls operation of the power source so as to drive the impeller at a set rotational speed and thus provide constant pumping action (blood flow).

Many patients who receive a blood pump are also provided with medication. Such medications may improve or regulate operation of the pump, such as a blood thinning medication or a vasodilator that may reduce the risk of thrombus formation in the pump. For such patients it is desirable to be able to ensure that the patient takes the prescribed medication, as well as to ensure that the medication has the desired effect on the patient's health. Furthermore, the fact that the patient is taking medication is yet additional information relating to the patient's condition and operation of the blood pump. It is also desirable to be able to better monitor the patient's health and the blood pump's operation using this additional data input.

SUMMARY

The present invention advantageously provides for a method of controlling an implantable blood pump of a living patient. The method includes receiving one or more pump signals indicating at least one from the group consisting of a motor speed of the blood pump, power supplied to the blood pump, and differential pressure exerted by the blood pump. One or more medication signals is received indicating whether the patient has taken a medication. The flow rate of blood based on a combination of the one or more pump signals and the medication signals is determined. At least one from the group consisting of increasing and decreasing power is supplied to the pump in response to the determined flow rate.

In another aspect of this embodiment, wherein determining the flow rate of blood based on the combination of the pump signals and the medication signals further includes selecting a flow rate function based on the one or more medication signals from among a plurality of flow rate functions mapping flow rate of the blood pump as a function of the one or more pump signals and determining the flow rate of blood using the selected flow rate function.

In another aspect of this embodiment, the at least one from the group consisting of increasing and decrease power supplied to the pump in response to the determined flow rate maintains operation of the pump at a given speed.

In another aspect of this embodiment, the one or more medication signals is indicative of a change in viscosity of the patient's blood, wherein the medication reduces viscosity of the patient's blood.

In another embodiment, a method for identifying the presence of an adverse health condition in a patient having an implanted blood pump includes receiving a first indication of a parameter of the blood pump at a first point in time. One or more medication signals is received indicating that the patient has taken a medication after the first point in time and before a second point in time. The parameter of the blood pump at the second point in time based at least in part on the first indication of the parameter and the one or more medication signals is predicted. A second indication of the parameter of the blood pump is received at the second point in time. The presence of an adverse health condition in the patient is identified if the parameter of the blood pump at the second point in time is greater than the predicted parameter by more than a threshold amount.

In another aspect of this embodiment, the parameter is an amount of power supplied to the blood pump.

In another aspect of this embodiment, the adverse health condition is thrombus.

In another aspect of this embodiment, predicting the parameter of the blood pump at the second point in time is further based on at least one of a clock signal indicating a time of day and an activity signal indicating a level of physical activity of the patient.

In another aspect of this embodiment, the method further includes generating an alert indicating that at least one from the group consisting of the patient has not taken the medication, the medication has not been effective, and an adverse health condition is present in the patient.

In another aspect of this embodiment, the one or more medication signals is indicative of a change in viscosity of the patient's blood, wherein the medication reduces viscosity of the patient's blood.

In another aspect of this embodiment, the one or more medication signals is indicative of dilation of the patient's vasculature, wherein the medication increases dilation of the patient's vasculature.

In another aspect of this embodiment, the one or more medication signals includes at a manual input from the patient indicating whether the patient took the medication.

In another embodiment, a signal processing circuit for identifying the presence of an adverse health condition in a patient having an implanted blood pump is configured to receive a first indication of a parameter of the blood pump at a first point in time. One or more medication signals is received indicating that the patient has taken a medication after the first point in time and before a second point in time. The parameter of the blood pump at the second point in time is predicted based at least in part on the first indication of the parameter and the one or more medication signals. A second indication of the parameter of the blood pump at the second point in time is received. The presence of an adverse health condition in the patient is identified if the parameter of the blood pump at the second point in time is greater than the predicted parameter by more than a threshold amount.

In another aspect of this embodiment, the parameter is an amount of power supplied to the blood pump.

In another aspect of this embodiment, the adverse health condition is thrombus.

In another aspect of this embodiment, the prediction of the parameter of the blood pump at the second point in time is further based on at least one of a clock signal indicating a time of day and an activity signal indicating a level of physical activity of the patient.

In another aspect of this embodiment, the signal processing circuit is further configured to generate an alert indicating that at least one from the group consisting of the patient has not taken the medication, the medication has not been effective, and an adverse health condition is present in the patient.

In another aspect of this embodiment, the one or more medication signals is indicative of a change in viscosity of the patient's blood, wherein the medication reduces viscosity of the patient's blood.

In another aspect of this embodiment, e one or more medication signals is indicative of dilation of the patient's vasculature, wherein the medication increases dilation of the patient's vasculature.

In another aspect of this embodiment, the one or more medication signals comprises a manual input from the patient indicating whether the patient took the medication.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present application provides for improved methods and control devices utilizing one or more medication inputs in order to ensure that the patient is taking medication is yet additional information relating to the patient's condition and operation of the blood pump, as well as to better monitor and evaluate operation of the pump and the patient's physiological health. At least certain aspects of the present application may be executed using a centrifugal pump, such as the HVAD® Pump manufactured by HeartWare Inc. in Miami Lakes, Fla., USA. The HVAD® Pump is further described in U.S. Pat. Nos. 6,234,772 and 8,512,013, the disclosures of which are incorporated by reference herein. Aspects of the disclosure may alternatively be executed by an axial flow pump, such as that used in the MVAD® ventricular assist device, also manufactured by HeartWare Inc. The MVAD® pump is further described in U.S. Pat. No. 9,339,598, the disclosure of which is incorporated by reference herein.

Figure 1:
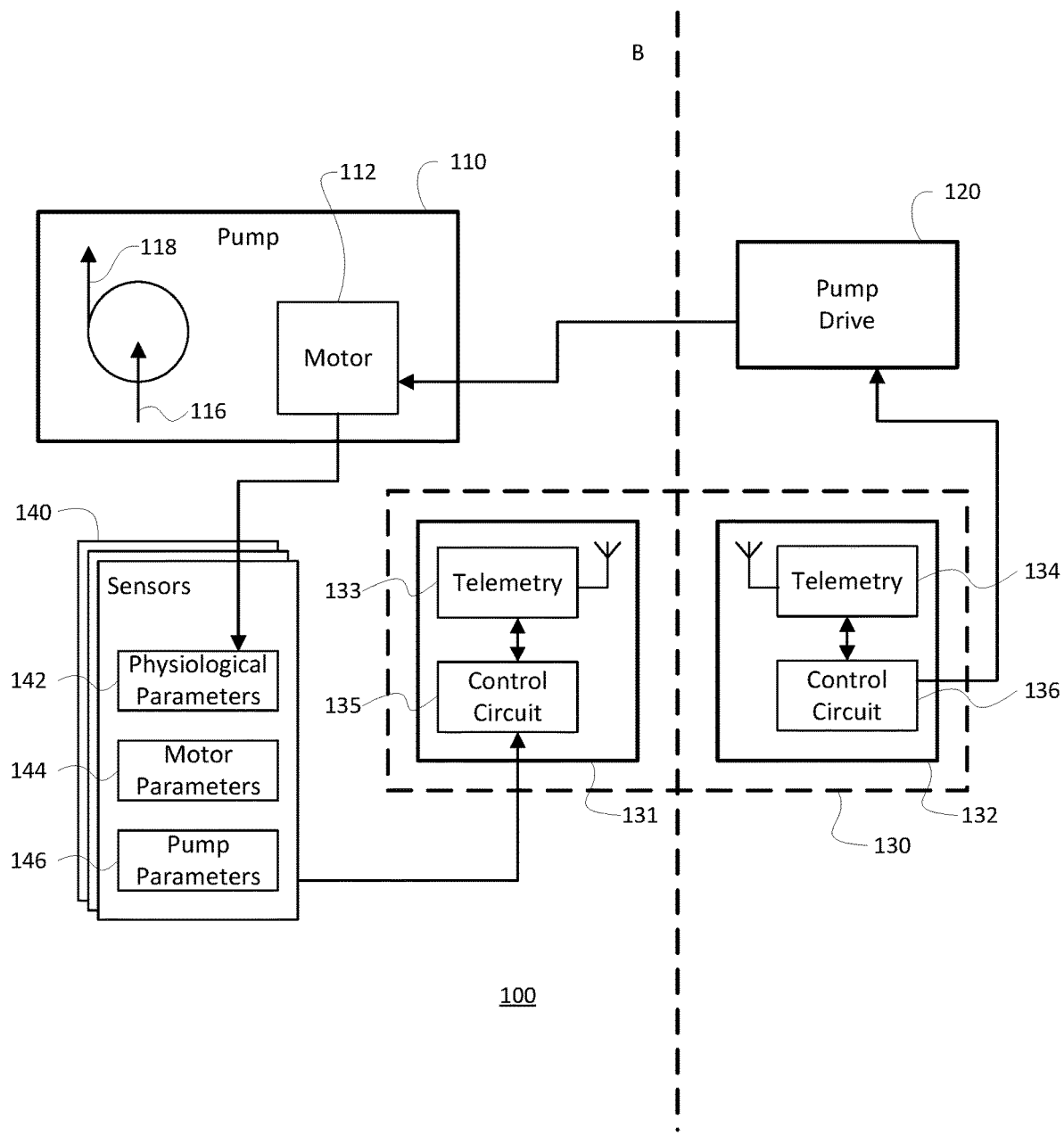
FIG. 1 is a diagrammatic view of an implantable blood pump system constructed in accordance with the principles of the present application.

Referring now to the drawings in which like reference designators refer to like elements, there is shown in FIG. 1 an implantable blood pump system 100 including a VAD, such as a rotary pump 110, incorporating a motor 112, that is implantable within the body B of a patient. The term "rotary pump" refers herein to a pump which incorporates a pumping element mounted for rotation in a housing. In one example, the system includes all of the features described in commonly owned U.S. Pat. No. 8,864,644, and copending and commonly owned PCT Application No. PCT/US2016/017148 and U.S. Patent Publication No. 2017/0112985, the disclosures of which are incorporated herein in their entirety.

The pump 110 may be a rotary impeller pump having an impeller mounted within a housing, so that the spinning motion of the impeller transfers momentum to the fluid to be pumped. Although the pump 110 and motor 112 are depicted as separate components for clarity of illustration in FIG. 1, in practice these components can be closely integrated with one another. For example, the impeller of the pump 110 may serve as the rotor of the motor 112.

The motor 112 may be a multi-phase brushless direct current, permanent magnet motor arranged to drive the impeller of the pump 110 at a rotational speed prescribed by the motor driver by means of a motor commutation technique such as trapezoidal commutation or other means. These components are arranged so that the pump 110 can be implanted within the body of a mammalian patient such as a human patient, with the inlet 116 in fluid communication with a ventricle of the heart, such as the left ventricle, and with the outlet 118 in fluid communication with an artery, such as the aorta. For example, the pump 110 may be arranged for implantation outside of the heart, and the inlet and outlet may include conduits that can be surgically connected to the ventricle and the aorta. In other arrangements, the pump 110 is arranged so that it may be implanted within the aorta and ventricle. Exemplary implantable pumps are described in detail in U.S. Pat. Nos. 6,264,635, 6,234,772 and 7,699,586; and US Patent Publication No.

2009/0112312. These patents and published patent applications, which are commonly assigned, are hereby incorporated by reference.

The system 100 may also include a pump drive circuit 120. The pump drive circuit 120 may include ports for one or more output connections and one or more input connections, an electrical storage battery and a motor driver to control the motor. The motor driver may include semiconductor switching elements which are responsive to control signals applied at a control input, so that the current supplied to motor 112 can be controlled. An output connection, such as a cable, may connect the pump drive circuit 120 to the motor 112 of pump 110, so that the motor driver can drive the motor 112 and thus operate the pump 110. In the example of FIG. 1, the pump drive circuit 120 is mounted outside of the patient's body B and is operatively connected to the motor 112 by one or more conductors that penetrate the skin of the patient. In other arrangements, the pump drive circuit may be implanted within the patient's body and may be connected to an external power source using inductive coupling or skin-penetrating conductors, such that the connection between the pump drive circuit and motor does not need to penetrate the patient's skin.

The system 100 may also include a signal processing circuit 130. In the example of FIG. 1, the signal processing circuit 130 is also a control circuit connected to the pump drive circuit 120 to control operation of the pump drive circuit 120, and thereby control operation of the pump 110. The signal processing circuit 130 is also connected to one or more sensors 140 to receive inputs from the sensors, such that operation of the pump may in turn be based on sensor data. In the example of FIG. 1, the signal processing circuit 130 includes both an internal module 131 implanted inside of the patient's body, and an external module 132 mounted outside of the patient's body B. The modules 131 and 132 may be connected to one another by a suitable signal transmitting arrangement, such as the radio frequency telemetry transmitting/receiving units 133 and 134 shown in FIG. 1, so that signals and data may be interchanged between the modules. Modules 131 and 132 may include conventional data processing elements such as one or more control circuits 135 and 136. The distribution of hardware elements and software functions between these control circuits 135 and 136 can vary. In one configuration, all of the data processing necessary to perform the monitoring and control methods described herein may be performed by the control circuit 136 of the external module 132, with the internal module 131 acting essentially as a conduit for relaying data and signals from the motor 110 to the external module 132 or vice versa. In another configuration, all of the data processing may be performed by the control circuit 135 of the internal module 131, with the external module acting essentially as a conduit for relaying data and signals from the internal module 131 to the pump drive circuit 120. In such an example, if the pump drive circuit is implanted within the patient's body, the external module 132 may be omitted entirely. Aside from the above examples, given the internal and external modules 131 and 132 capability to relay data and signals between one another, it is well within the ability of those skilled in the art to provide for some data processing to be performed by the control circuitry of one module, while the remaining data processing is performed by the control circuitry of the other module.

The internal module 131 may be connected to receive power from the alternating current supplied by the pump drive circuit 120 to motor 112. The power required to operate the circuitry of the internal module 131 is typically about 3 orders of magnitude less than the power required to drive motor 112. This arrangement is particularly useful where the internal module 131 is physically located in the vicinity of the pump 110, such as being physically coupled to and/or housed in a housing of the pump. In such cases where the internal module 131 of the signal processing circuit 130 is physically located in the vicinity of the pump 110, it may be desirable to provide magnetic shielding between the coils of the pump motor 112 and the circuitry of the internal module 131. In other arrangements, the internal module 131 may be positioned apart from the pump 110. In such arrangements, the signal processing circuitry 130 may receive power from an internal battery (not shown), such as a primary battery or rechargeable battery.

The sensors 140 of the system 100 may include one or more sensors for measuring blood flow and circulation through the patient's cardiovascular system. For example, the one or more sensors may indicate a physiological parameter 142 indicative of blood flow being output by a ventricle of the patient's heart. Additionally or alternatively, one or more sensors may indicate motor parameters 144, such as motor speed or angular position (phase), or back electromotive force ("back EMF" or "BEMF") of the pump, and/or pump parameters 146 such as flow rate of blood exiting the pump and/or pressure differential across the pump. In some instances, a control circuit 135 and/or 136 may be programmed to determine these features non-invasively based on other parameters of the pump (e.g., determining flow rate based on differential pressure, motor current and/or BEMF). Examples of flow rate and pressure determinations based on BEMF are described in detail in US Patent Publication Nos. 2012/0245681, 2014/0100413, 2014/0357937. These patents and published patent applications, which are commonly assigned, are hereby incorporated by reference.

Figure 2:
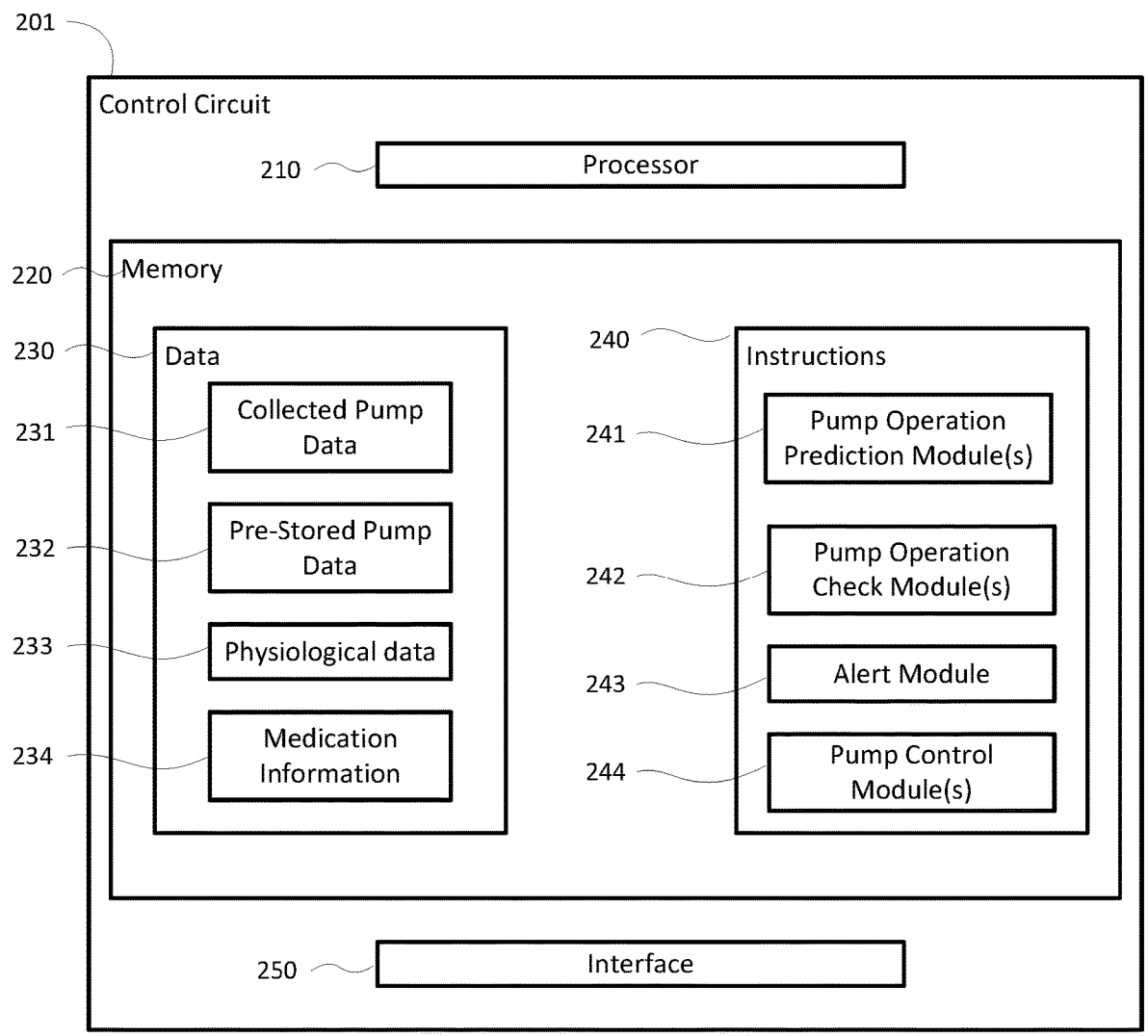
FIG. 2 is a block diagram of an example signal processing circuit of the implantable blood pump system shown in FIG. 1.

Referring now to FIG. 2, a signal processing circuit 201 may include a processor 210. The processor 210 may be hardware that performs one or more operations of the present application. By way of example only, one or more control units (not shown) coupled to an arithmetic logic unit (ALU) (not shown) and memory 220 may direct the signal processing circuit 201 to carry out program instructions 240 stored in memory 220 at a particular clock rate. The processor 210 may be any standard processor, such as a central processing unit (CPU), or a dedicated processor, such as an application-specific integrated circuit (ASIC), a field programmable gate array (FPGA) or a microprocessor. While one processor block is shown, the signal processing circuit 201 may also include multiple processors which may or may not operate in parallel.

Memory 220 stores information accessible by processor 210 including instructions 240 for execution by the processor 210 and data 230 which is retrieved, manipulated or stored by the processor 210. The memory 220 may be of any type capable of storing information accessible by the processor, such as a hard-drive, ROM, RAM, CD-ROM, write-capable, read-only, or the like.

Data 230 may be retrieved, stored or modified by processor 210. Although the data of the present disclosure is not limited by any particular data structure, the data 230 may be stored in computer registers, in a relational database as a table having a plurality of different fields and records, such as an XML. The data 230 may also be formatted in any computer readable format such as, but not limited to, binary values, ASCII or EBCDIC (Extended Binary-Coded Decimal Interchange Code). Moreover, any information sufficient to identify the relevant data may be stored, such as descriptive text, proprietary codes, pointers, or information which is used by a function to calculate the relevant data.

The data 230 may include data received from one or a combination of the sensors described herein. By way of example, such data may include regularly collected pump data 231 (e.g., flow rate, differential pressure, pump speed, BEMF, etc.) pre-stored pump data 232 (e.g., flow-pressure curves), physiological data 233 (e.g., hematocrit level) and medication information 234 (e.g., type of medication taken by patient, dosage information, etc.). In the case of flow rate measurements, in some examples, the flow rate measurements may themselves be determined based on other stored data (e.g., BEMF, flow-pressure curves).

The instructions 240 may include any set of instructions to be executed directly (such as machine code) or indirectly (such as scripts) by the processor 210. In that regard, the terms "instructions," "steps" and "programs" may be used interchangeably herein. The instructions 240 may include one or more modules for analyzing or processing the received data. For example, a pump operation prediction module 241 may perform various analyses of the data 230 in order to predict an expected parameter of the pump, such as power to be supplied to the pump in order to maintain operation of the pump at a given output. The instructions 240 may also include a pump operation check module 242 for determining whether the pump is operating in the manner predicted by the prediction module 241. When pump operation is not as predicted or expected, it may be an indication of pump failure, a problem with the patient's medication, or an adverse health condition for the patient. The instructions 240 may also include an alert module 243 to notify the patient and/or a clinician of such unexpected operation and the above unwanted conditions.

The instructions 240 may further include a pump operation module 244 for operating the pump. The pump operation module 244 may rely on the analyzed data 230 to determine changes to the pump operation parameters in order to maintain a given pump output. For instance, if the signal processing circuit 201 receives an indication that the patient has taken a medicine that tends to reduce viscosity of the patient's blood, then the pump operation module may instruct the drive circuit to reduce power supplied to the pump, as less power will typically be needed to maintain the pump at its previous operating point. In this regard, the pump operation module 244 closes a feedback control loop for maintaining a parameter of the pump (such as pump speed, or power supplied to the pump) at a predetermined value.

The signal processing circuit 201 includes one or more interfaces 250 for connecting to inputs (e.g., sensors 140) and outputs (e.g., pump drive circuit 120). The interfaces 250 may include wired and/or wireless connections (e.g., Bluetooth). For components of the signal processing circuit 201 that are adapted to be disposed within the body of the patient, the interface 250 may include known elements for communicating signals through the skin of the patient.

The example devices described above may be operated using the example methods described herein. It should be understood that the operations of the following methods do not have to be performed in the precise order described below. Rather, various operations can be handled in a different order, or simultaneously. Moreover, operations may be added or omitted.

Figure 3:
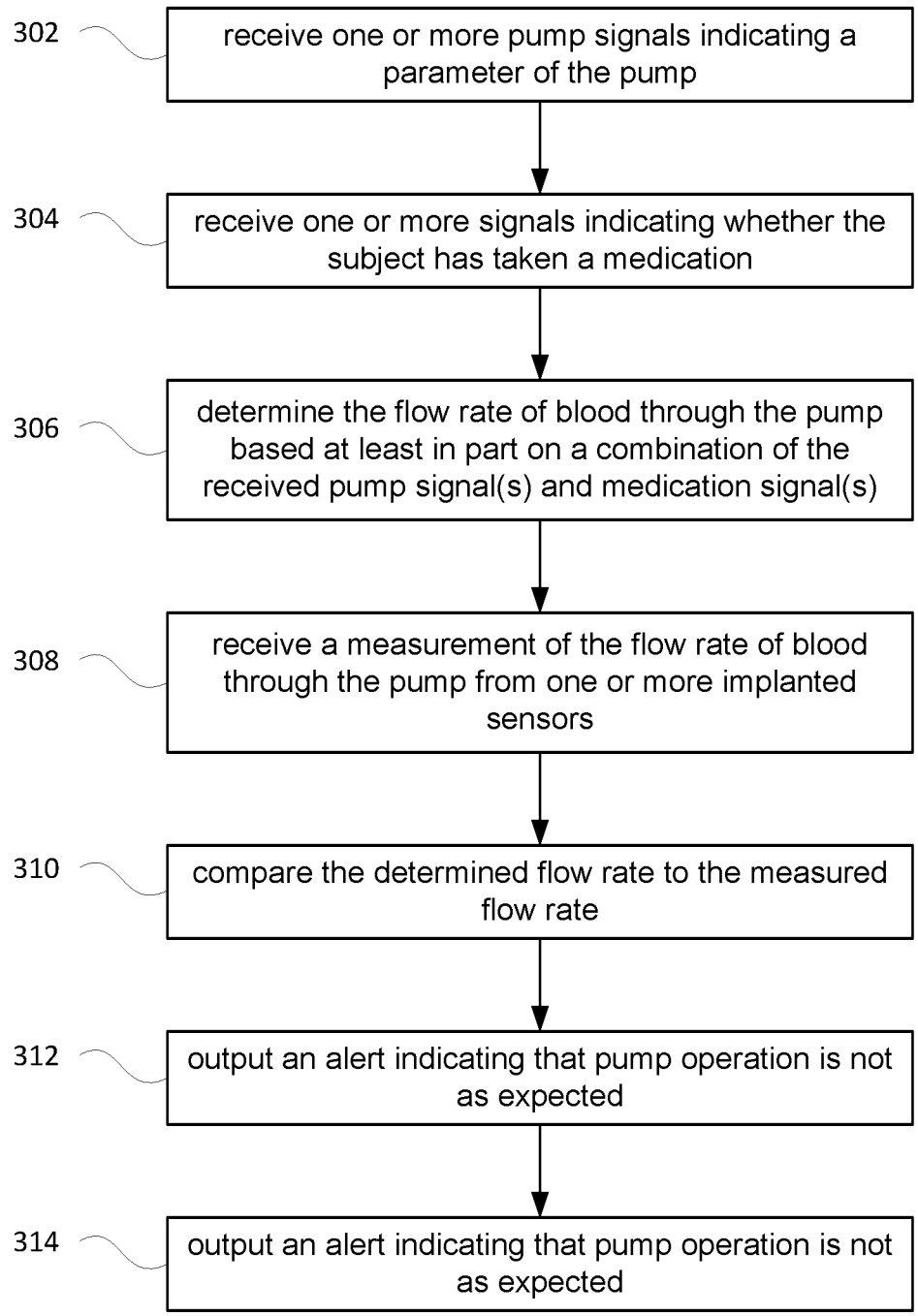
FIG. 3 is a flow chart of a method for determining a flow rate of blood through the pump using medication information.

Now referring to FIG. 3, flow diagram 300 shows an example method for the signal processing circuit 201 of an implantable blood pump to determine a flow rate of blood through the pump using medication information. At step 302, the signal processing circuit 201 receives one or more pump signals indicating a parameter of the pump. The pump parameter may be, for example, a motor speed of the pump, power supplied to the pump, and differential pressure exerted by the pump. At step 304, the signal processing circuit 201 receives one or more signals indicating whether the patient (e.g., in whom the pump is implanted) has taken (i.e., orally or intravenously) a medication. The medication signal may indicate the type and dose/quantity of medication taken by the patient. The medication may have a known or expected effect on operation of the pump, such as changing the viscosity of the patient's blood. For instance, if the medication is a blood thinner, it can be expected that the viscosity of the patient's blood decreases, in which case the flow rate of blood (for an equal amount of power supplied to the pump) would likely increase. Similarly, if the medication is a vasodilator, it can be expected that the flow rate of blood increases, and that pressure exerted by the pump would likely decrease.

The medication signal may be provided manually by the patient (e.g., press a button indicating that a recommended dosage of medication has been taken, manually entering the medication and dosage taken). Alternatively, the medication signal may be transmitted automatically to the signal processing circuit 201. For instance, the medication may be contained in a smart dispenser or smart case (not shown). The smart dispenser or smart case may include sensors to detect when the patient has taken the medication (e.g., pressing of a dispense button on the smart dispenser/case, opening the smart dispenser/case). The smart dispenser or smart case may also include sensors capable of detecting how much medication is dispensed (e.g., based on change in volume, weight, or pressure, based on a mechanical sensor, etc.).

At step 306, the signal processing circuit determines the flow rate of blood through the pump based at least in part on a combination of the received pump signal(s) and medication signal(s). In one example, the signal processing circuit may access any one of a plurality of flow rate functions to execute the flow rate determination. The flow rate functions may map flow rate through the blood pump as a function of one or more pump parameters, such as an HQ curve that maps flow (Q) as a function of differential pressure (H), or such as a current-flow curve that maps flow as a function of current supplied to the motor, or such as a back electromotive force (BEMF)—flow curve that maps BEMF as a function of flow, for instance as described in commonly owned U.S. Publication No. 2012/0245681, the disclosure of which is incorporated by reference herein in its entirety. The mapping of flow against any of the above example parameters may be further dictated by a speed of the pump and/or viscosity of the blood flowing through the pump (e.g., hematocrit level of the blood). Therefore, the signal processing circuit is capable of accessing multiple functions, each mapping flow rate for a different given pump speed and/or blood viscosity. The medication signal may be utilized by the signal processing circuit to determine the expected viscosity of the blood, such that the medication signal may indicate which of the multiple functions should be selected for determining the flow rate of blood.

Optionally, the signal processing circuit 201 may test the flow rate determination and generate an alert if the test results in a failure. At step 308, the signal processing circuit 201 may also receive a measurement of the flow rate of blood through the pump from one or more implanted sensors. At step 310, the determined flow rate (from 306) may be compared to the measured flow rate (from 308). If the compared values are within a predetermined value or percentage margin of error, then the comparison indicates that the patient has taken the medication, that the medication has affected the patient's blood in the predicted or expected manner, and that operation of the pump has been modified in a predicted or expected manner. However, if there is a unpredicted difference between the determined and measured flow rates, the unpredicted difference may indicate either that the patient has not taken the medication, or that the medication has not been effective (e.g., a blood thinner has not thinned the patient's blood, the patient's blood is thinner but there is still potential for thrombus formation), or that the pump is not operating correctly. At step 312, the signal processing circuit 201 may further control the generation of an alert (e.g., visual alert on a display, audio alert, transmission of a message over a network for example to a clinician) indicating that pump operation is not as expected. The alert may prompt the patient to be examined, such as to make sure that the patient is in fact taking the medication at the proper dosage, to make sure that the medication is working, to ensure that the patient does not have an adverse health condition causing the unpredicted difference and/or to ensure that the pump is operating correctly.

Optionally, at step 314, the signal processing circuit 201 may further control a change to an operating parameter of the pump in response to the medication signal. For instance, once it has been determined that the patient has taken a medication, and that the medication will affect the pump's operation (e.g., due to a change in a properties of the blood, due to a change in a property of the patient's vasculature), the signal processing circuit 201 may instruct the pump drive circuit to increase or decrease power supplied to the pump. The change in power supplied to the pump may result in an operation of the pump being maintained at a given set point, such as at a given speed.

Figure 4:
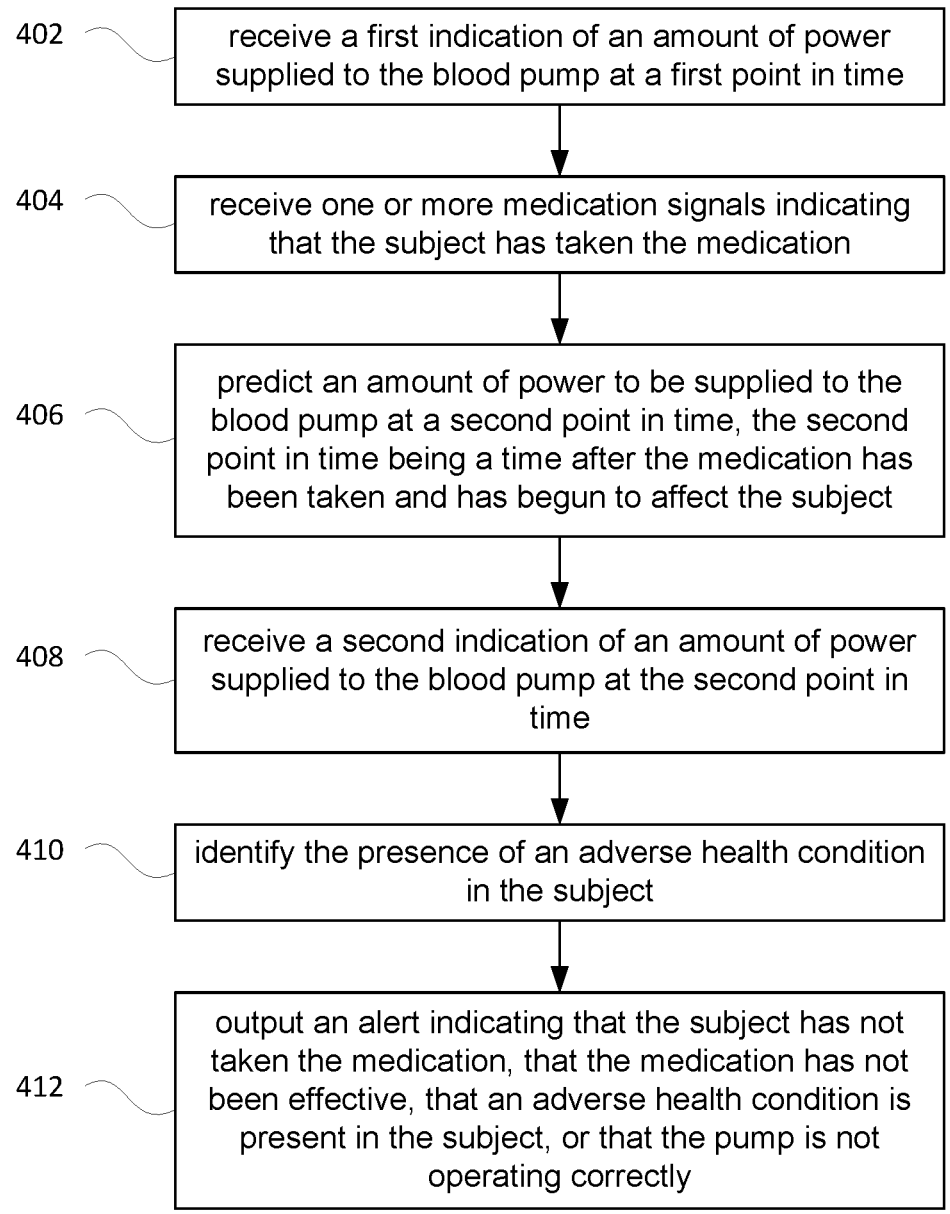
FIG. 4 is a flow chart of a method for identifying the presence of an adverse health condition in a patient having an implantable blood pump.

Referring now to FIG. 4, flow diagram 400 shows an example method for the signal processing circuit 201 of an implantable pump to identify the presence of an adverse health condition in a patient into whom the pump is implanted. Unlike in the example of FIG. 3, the example of FIG. 4 does not necessarily require a determination of flow rate in order to identify the presence of an adverse health condition of the patient.

At step 402, the signal processing circuit 201 receives a first indication of an amount of power supplied to the blood pump at a first point in time. The amount of power supplied may be determined by current or voltage measurements made by a sensor coupled to both the signal processing circuit and the line over which power is supplied to the pump. The first point of time is generally a point of time preceding the patient's having taken a medication. However, it is possible that the first point of time may be during the taking of the medication or immediately after the taking of the medication, so long as it may be ensured that the medication has not yet affected the condition of the patient.

At step 404, the signal processing circuit 201 receives one or more medication signals indicating that the patient has taken the medication. As in the example of FIG. 3, the medication signal may be provided automatically or manually, and may indicate the type and dosage of a medication having a known or expected effect on operation of the pump. For instance, in the case of a blood thinner for which it can be expected that the viscosity of the patient's blood will decrease, or the case of a vasodilator for which it can be expected that the resistance against blood flow will decrease, the amount of power needed to pump the same amount of blood will generally remain the same or decrease.

At step 406, the signal processing circuit 201 predicts an amount of power to be supplied to the blood pump at a second point in time, the second point in time being a time after the medication has been taken and has begun to affect the patient (and thereby, operation of the pump). The predicted amount of power may be based on a previous indication of an amount of power being supplied before the medication was taken. In some cases, the predicted amount of power may simply be equal to the previous amount of power (e.g., a prediction that no more than the previous amount of power will be needed).

At step 408, the signal processing circuit 201 receives a second indication of an amount of power supplied to the blood pump at the second point in time. This second indication may be compared to the predicted amount of power to determine whether the pump is operating as expected. Alternatively, the second indication may be compared to the first indication.

At step 410, the signal processing circuit identifies the presence of an adverse health condition in the patient. For instance, if the patient takes a blood thinner or vasodilator but the amount of power required to operate the pump increases (or alternatively, if the amount of power does not decrease), it may be an indication of an adverse health condition in the patient, such as thrombus formation. The identification of an adverse health condition may require the increase in power to be at least by a predetermined threshold amount. In other instances, instead of monitoring power required to operate the pump, a different condition of the patient or pump may be monitored. Such conditions may include changes in blood volume, bleeding, hemorrhage, red blood cell damage, or a problematic change in blood pressure.

With regard to monitoring power, the amount of power needed to maintain blood flow at a consistent rate may change over the course of time. For example, blood flow may increase when the patient is active or awake (as compared, for instance to an inactive or sleeping patient), which may affect the amount of power needed to maintain a certain flow rate. Thus, in some examples, the amount of power supplied to the pump may change regardless of the medication taken by the patient. To better predict the amount of power that will be supplied to the pump at a given time, the signal processing circuit may include or be capable of accessing a clock signal indicating a time of day and/or an activity signal (e.g., heart rate, respiratory rate, etc.) indicating a level of physical activity of the patient. In such examples, the signal processing circuit 201 may predict the amount of power at the second point in time based further on the clock signal and/or activity signal.

Optionally, at step 412, if the presence of an adverse health condition is identified, the signal processing circuit 201 may control the output of an alert (similar to the alerts described in connection with FIG. 3) to indicate that the patient has not taken the medication, that the medication has not been effective, that an adverse health condition is present in the patient, or that the pump is not operating correctly.

In those instances where the patient has not taken the medication, or where the dosage of the medication in the patient's body has decreased (e.g., due to the medication's half-life) the alert may be resolved simply by the patient taking or increasing a dosage of the medication. If the patient has taken the medication at the proper dosage but the medication has not been successful, it may be necessary for a clinician to examine the patient for any adverse health conditions, such as thrombus formation.

Figure 5:
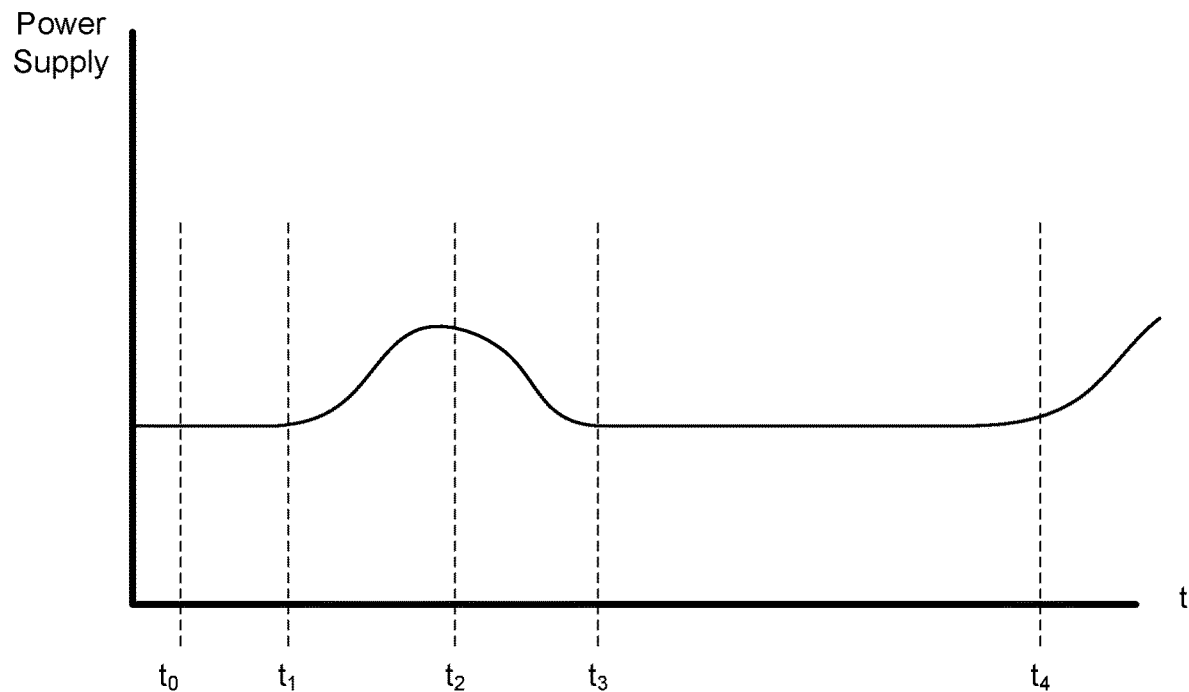
FIG. 5 is a graph showing the supply of power over time to a blood pump using the method shown in FIG. 4.

Referring now to FIG. 5, at time t₀, the power level is steady, indication that the patient's medication is working correctly. At time $t_1$, the power level increases. The change in slope may indicate that the patient's medication has begun to stop working, and the signal processing circuit may alert the patient accordingly. In response, the patient may take the proper dosage of the medication. At time $t_2$, the medication has begun working and the pump can reduce its work, thereby reducing the amount of power supplied to the pump back to the previous, steady level (which is reached at time $t_3$). At time $t_4$, the power level again increases, and the process begins again, with the patient taking another dosage of the medication. If after the medication has been taken the power level continues to rise and does not fall, the patient may need to be examined by a clinician to determine whether a possible adverse health is causing the increase in power.

While the above examples specifically describe using a blood thinner or vasodilator as an input to monitor pump operation or detect an adverse health condition, those skilled in the art will recognize that the same or similar methods may be performed for other any kind of medication that would result in a predictable change to a parameter of the pump or the patient's vasculature. Such medication may include as antiplatelet drugs or antiaggregants, blood pressure medications, and so on.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A method for identifying the presence of an adverse health condition in a patient having an implanted blood pump, comprising:
   receiving a first indication of a parameter of the blood pump at a first point in time;
   receiving two or more signals to indicate that the patient has taken a medication, the two or more signals including:
      a manual input from the patient indicating that the patient has taken the medication after the first point in time and before a second point in time; and
      a physiological parameter signal indicating that a physiological response has occurred in response to the medication;
   predicting the parameter of the blood pump at the second point in time based at least in part on the first indication of the parameter and the two or more signals;
   receiving a second indication of the parameter of the blood pump at the second point in time;
   identifying the presence of an adverse health condition in the patient if the parameter of the blood pump at the second point in time deviates from the predicted parameter by more than a threshold amount; and
   generating an alert indicating that at least one from the group consisting of the patient has not taken the medication, the medication has not been effective, and an adverse health condition is present in the patient.

2. The method of claim 1, wherein the parameter is an amount of power supplied to the blood pump.

3. The method of claim 1, wherein the adverse health condition is thrombus.

4. The method of claim 1, wherein predicting the parameter of the blood pump at the second point in time is further based on at least one of:
   a clock signal indicating a time of day; and
   an activity signal indicating a level of physical activity of the patient.

5. The method of claim 1, wherein at least one of the two or more signals is indicative of a change in viscosity of the patient's blood, wherein the medication reduces viscosity of the patient's blood.

6. The method of claim 1, wherein at least one of the two or more signals is indicative of dilation of the patient's vasculature, wherein the medication increases dilation of the patient's vasculature.

7. A system for identifying the presence of an adverse health condition in a patient having an implanted blood pump, the system comprising:
   two or more sensors;
   a signal processing circuit coupled to the two or more sensors, the signal processing circuit configured to:
      receive from one of the two or more sensors a first indication of a parameter of the blood pump at a first point in time;
      receive from one of the two or more sensors two or more signals indicating that the patient has taken a medication after the first point in time and before a second point in time, the two or more signals including:
         a manual input from the patient indicating that the patient has taken the medication; and
         a physiological parameter signal indicating that a physiological response has occurred in response to the medication; and
      predict the parameter of the blood pump at the second point in time based at least in part on the first indication of the parameter and the two or more signals;
      receive from one of the two or more sensors a second indication of the parameter of the blood pump at the second point in time;
      identify the presence of an adverse health condition in the patient if the parameter of the blood pump at the second point in time deviates from the predicted parameter by more than a threshold amount; and
      generate an alert indicating that at least one from the group consisting of the patient has not taken the medication, the medication has not been effective, and an adverse health condition is present in the patient.

8. The system of claim 7, wherein the parameter is an amount of power supplied to the blood pump.

9. The system of claim 7, wherein the adverse health condition is thrombus.

10. The system of claim 7, wherein the prediction of the parameter of the blood pump at the second point in time is further based on at least one of:
    a clock signal indicating a time of day; and
    an activity signal indicating a level of physical activity of the patient.

11. The system of claim 7, wherein the two or more signals is indicative of a change in viscosity of the patient's blood, wherein the medication reduces viscosity of the patient's blood.

12. The system of claim 7, wherein the two or more signals is indicative of dilation of the patient's vasculature, wherein the medication increases dilation of the patient's vasculature.

* * * * *